(12) United States Patent
Kusunoki et al.

(10) Patent No.: US 8,236,530 B2
(45) Date of Patent: Aug. 7, 2012

(54) METHOD FOR PREPARING MONOCLONAL ANTIBODY

(75) Inventors: Chihiro Kusunoki, Takatsuki (JP); Atsushi Fukushima, Yokohama (JP)

(73) Assignees: Japan Tobacco Inc., Tokyo (JP); Abgenix, Inc., Fremont, CA (US)

( * ) Notice: Subject to any disclaimer, the term of this patent is extended or adjusted under 35 U.S.C. 154(b) by 1499 days.

(21) Appl. No.: 11/238,983

(22) Filed: Sep. 28, 2005

(65) Prior Publication Data

US 2006/0059575 A1    Mar. 16, 2006

Related U.S. Application Data

(63) Continuation of application No. 09/937,495, filed as application No. PCT/JP00/02022 on Mar. 30, 2000, now abandoned.

(30) Foreign Application Priority Data

Mar. 30, 1999    (JP) ...................................... 11-87929

(51) Int. Cl.
*C12P 21/04* (2006.01)
*C12N 5/00* (2006.01)
*C12N 15/08* (2006.01)

(52) U.S. Cl. ........................... 435/70.21; 35/326; 35/455

(58) Field of Classification Search ... 800/6; 435/70.21, 435/326, 455
See application file for complete search history.

(56) References Cited

U.S. PATENT DOCUMENTS

| | | | |
|---|---|---|---|
| 6,475,787 B1 | 11/2002 | Wood et al. | |
| 2003/0153039 A1 | 8/2003 | Wood et al. | |

FOREIGN PATENT DOCUMENTS

| | | |
|---|---|---|
| WO | WO87/04462 A1 | 7/1987 |
| WO | WO 93/12227 A | 6/1993 |

OTHER PUBLICATIONS

Kipriyanov et al, (Molecular Biotechnology, 12: 173-201, 1999).*
Hamers-Casterman et al, (Nature, 363: 446-448, 1993.*
Spinelli et al, (Biochemistry, 39: 1217-1222, 2000).*
Kipriyanov et al (Immunology Today, 21(8): 364-370, 2000.*
Dorai et al (The Journal of Immunology, 139(12): 4232-4241, 1987).*
Dorai et al (Hybridoma, 11(5): 667-675, 1992).*
Green et al, (Journal of Immunological Methods 231: .11-23, 1999).*
Mocikat et al, (Immunology, 84: 159-163, 1995).*
Abbas et al., (1994) Cellular and Molecular Immunology $2^{nd}$ ed., W.B Saunders Co., 1-457.
Green et al., (1994) Antigen-specific human monoclonal antibodies from mice engineered with human Ig heavy and light chain YACs. Nature Genetics. 7:13-21.
Margulies et al., (2005) Monoclonal Antibodies: Producing Magic Bullets by Somatic Cell Hybridization J. Immunology. 174:2451-2452.
Mendez et al., (1997) Functional transplant of megabase human immunoglobulin loci recapitulates human antibody response in mice. Nature Genetics. 15:146-186.
Ochi et al., "Functional immunoglobulin M production after transfection of cloned immunoglobulin heavy and light chain genes into lympoid cells" *Proc. Natl. Acad. Sci. USA* 80:6351-6355 (Oct. 1983).
Wells et al., (1999) Transgene vectors go retro. Nature Biotechnology. 17:25-6.

* cited by examiner

*Primary Examiner* — Gerald Leffers, Jr.
*Assistant Examiner* — Magdalene Sgagias
(74) *Attorney, Agent, or Firm* — James S. Keddie; Bozicevic, Field & Francis LLP

(57) ABSTRACT

A significantly increased amount of a monoclonal antibody is obtained from the culture medium of recombinant hybridoma prepared by introducing genes encoding a protein identical to the immunoglobulin heavy chain polypeptide of the specific monoclonal antibody into an immortalized B cell (hybridoma) producing the monoclonal antibody.

5 Claims, 2 Drawing Sheets

Structure and restriction enzyme map of pDH502

METHOD FOR PREPARING MONOCLONAL ANTIBODY

CROSS-REFERENCE

This application is a continuation application of Ser. No. 09/937,495, filed Feb. 28, 2002 which is a 371 National Phase of International Application No. PCT/JP00/02022 filed Mar. 30, 2000 (Publication No. WO 00/058499) which claims priority to Japanese Patent Application Serial No. 1187929 filed Mar. 30, 1999, which applications are incorporated herein by reference in their entirety and to which applications we claim priority.

TECHNICAL FIELD

The present invention relates to a method for preparing monoclonal antibodies, specifically, a method for increasing the monoclonal antibody amount secreted from cells, and the cells prepared by the method.

BACKGROUND ART

The living body of a mammal possesses humoral immunity which is a defense system for specifically capturing and eliminating various antigens (for example, exogenous antigens (viruses, bacterial toxins, and chemical substances), or autoantigens (for example, autoreactive lymphocytes; cancer cells; excessive endogenous factors (cytokines, hormones, or growth factors)) which are detrimental for maintaining homeostasis in the living body and can become causatives (pathogens) that cause or deteriorate various diseases. In this humoral immunity, the so-called antibodies (also called immunoglobulins) play a major role.

An antibody (immunoglobulin) has a Y-shaped basic structure comprising four polypeptide chains—two long polypeptide chains (immunoglobulin heavy chains; IgH chains) and two short polypeptide chains (immunoglobulin light chains; IgL chains). This Y-shaped structure is made when the two IgH chains bridged by disulfide bonds are connected to each of the IgL chains through another disulfide bond.

Due to this function of capturing and eliminating an antigen (pathogen) harmful to the living body, antibodies have been used as drugs for a long time. An early antibody drug was the so-called antiserum, and serum itself in which various types of antibodies against a specific antigen (for example, bacterial toxins and snake poison) are present (in other words, it was a polyclonal antibody) was used. The method for obtaining this antiserum however was limited to collecting from serum, and therefore, the supply was inevitably limited. Moreover, it was extremely difficult to isolate a single type of antibody molecule comprising specificity to a specific antigen, namely a monoclonal antibody, from this antiserum.

The successful preparation of a monoclonal antibody using hybridoma by Kohler and Milstein in 1975 (Nature, Vol. 256, p. 495-497, 1975) led to the solution of these problems.

Specifically, in this method, immortalized B cells (hybridoma) were obtained by fusing cells producing a monoclonal antibody of a specific type (B cells such as splenocytes) collected from a non-human mammal immunized by an antigen with myeloma cells, and thus immortalizing the cells. Then, the monoclonal antibody is purified after culturing the hybridoma. This method does not necessarily achieve mass-production of a desired monoclonal antibody, however, is a dramatic method as the desired monoclonal antibody can be obtained when it is desired. This technique enabled the use of monoclonal antibodies as drugs.

Monoclonal antibodies have been used as extremely useful drugs for preventing and treating various diseases due to their exceptional superiority in antigen specificity and stability in comparison to the above antiserums (polyclonal antibodies). They are also superior in their capability to control the biological activity of an antigen (for example, inhibition of activity, enhancement of activity, inhibition of signal transduction., signal transduction in place of ligands, or inhibition of intercellular adhesion) by specifically binding to the antigen (for example, exogenous antigens such as viruses and bacterial toxins; various endogenous factors such as cytokines, hormones, and growth factors, molecules on the cell surface such as receptors, cell adhesion molecule, and signal transduction molecules) involved in the onset or deterioration of diseases.

On the other hand, the amount of monoclonal antibody produced by the above hybridoma is not necessarily large, and it was difficult to produce a large amount of a monoclonal antibody by culturing the hybridoma and purifying and isolating the monoclonal antibody from the cell culture solution. Therefore, methods for producing a larger amount of monoclonal antibodies are being studied in order to cheaply supply a sufficient amount of monoclonal antibodies, which are extremely useful as drugs.

For example, it has been reported that antibody production increases when human antibody-producing hybridomas are cultured in an interleukin 2-supplemented culture medium (Cellular immunology, vol. 115, p. 325-333, 1988).

In addition, in an attempt using the genetic engineering technique, Ochi et al. have reported as follows (Proc. Natl. Acad. Sci. USA Vol. 80, p. 6351, 1983):

Recombinant cells obtained by introducing IgH chain gene ($\mu$) and IgL chain gene ($\kappa$) encoding the IgH chain and IgL chain ($\kappa$), respectively, of an anti-hapten (TNP; 2,4,6-trinitrophenyl) monoclonal antibody, which were cloned from hybridoma Sp6 which produces mouse IgM monoclonal antibody specific to TNP into plasmacytoma X63Ag8 which produces a IgG monoclonal antibody against an unknown antigen different from the anti-TNP monoclonal antibody, produce both the anti-TNP antibody and the IgG antibody. Moreover, recombinant cells obtained by introducing IgH gene encoding the heavy chain of the anti-TNP antibody into mutant cells that derive from hybridoma Sp6 and secrete solely X chain, the light chain of the TNP antibody, but do not express the heavy chain and thus do not secrete the anti-TNP antibody as a result, produce the anti-TNP antibody.

However, the experiment of Ochi et al. failed to increase the amount of monoclonal antibody secreted, since the amount of anti-TNP-antibody produced by each of the above recombinant cells is about 10 to 25% of the amount of anti-TNP antibody produced by hybridoma Sp603 sub-cloned from the hybridoma Sp6.

In general, as a means to produce a large amount of a monoclonal antibody by hybridoma and host cells into which the antibody gene has been inserted, the method of increasing the number of cells per culture solution and the method of improving the production of a substance per cell have been studied.

The method of increasing the number of cells per culture solution is preferable, however, the increased number of cells does not necessarily lead to a high production of an antibody. It is important to select and isolate a single cell line with a high antibody productivity and culture the single cell line. Selection and isolation of cell lines with high antibody productivity (for example, hybridoma and recombinant cells) are laborious, but are extremely important factors for the purpose of increasing the productivity of cells producing a desired monoclonal antibody.

On the other hand, in the production of a desired protein using recombinant cells, the following method is used to increase the expression efficiency of a desired protein-encoding gene introduced into recombinant cells, and thus, increase the production of the desired protein. Namely, dihydrofolate reductase (DHFR) gene or glutamate synthase (GS) gene is introduced together with the gene encoding the desired protein into the recombinant cells to increase the copy number of the gene of the desired protein (for example, WO81/02426 and WO87/04462).

Taking the DHFR gene as an example, in these methods, specifically, an expression vector is constructed in which DHFR gene has been inserted near the gene encoding a desired protein, host cells are transformed with the expression vector, and drug-resistant lines are selected by culturing the host cells in the presence of a drug (for example, methotrexate (MTX), phosphinotricine, methionine sulfoximine).

In the obtained drug-resistant strains, the copy number of the introduced dhfr gene is increased (gene-amplified) and flanking genes are also amplified at the same time. It can be expected that, as a result of the amplified copy number of the gene encoding the desired protein, the desired protein production will also be increased.

In immortalized B cells (for example, hybridoma obtained by fusing the above B cells and myeloma cells) obtained by immortalizing monoclonal antibody-producing B cells isolated from a mammal immunized by an antigen, both the rearranged immunoglobulin heavy chain gene (IgH gene) and the rearranged immunoglobulin light chain gene (IgL gene) have been incorporated into the genome.

In order to amplify the IgH and IgL genes by the above gene-amplification gene, it is necessary to identify the location of each gene on the genome and to insert the gene-amplification gene near each gene.

This method is theoretically possible, however, it requires enormous time and labor and it is impossible to target the gene-amplification gene at a desired location on the genome of the immortalized B cells.

DISCLOSURE OF THE INVENTION

The present invention aims to definitely improve the productivity of monoclonal antibody producing cells, especially immortalized B cells (hybridoma), by a more convenient manipulation. Specifically, the objective is to provide a novel method capable of improving the expression efficiency of a monoclonal antibody by immortalized B cells (hybridoma), which was until now considered to be difficult.

The present inventors focused on the fact that in the production of monoclonal antibodies by hybridoma, the expression of immunoglobulin heavy chain gene (IgH chain gene) is often instable in comparison to that of immunoglobulin light chain gene (IgL chain gene), and the secretion of antibody molecules occasionally comes to a halt. The inventors conceived that the secreted amount of antibody molecules depends on the expression amount of the IgH chain gene.

Based on this idea, the present inventors zealously studied methods for improving the secretion amount of antibody molecules by improving (enhancing) the expression of IgH chain gene. As a result, it was found the amount of monoclonal antibody secreted is significantly increased in recombinant hybridoma obtained by introducing the IgH encoding cDNA (comprising a nucleotide sequence identical to the rearranged endogenous IgH gene encoding the heavy chain polypeptide of the monoclonal antibody) cloned from immortalized B cells (hybridoma) into the hybridoma producing the specific monoclonal antibody. It was further revealed that the amount of monoclonal antibody produced could also be increased by introducing a gene-amplification gene such as DHFR gene with the IgH encoding cDNA into the hybridoma, to complete the present invention.

By using the method of the present invention, the amount of monoclonal antibodies produced by monoclonal antibody-producing cells can be significantly increased. Specifically, the method of the present invention for producing a monoclonal antibody, and cells produced by the method, are extremely useful for producing monoclonal antibodies useful as drugs.

Specifically, the present invention relates to the following methods and cells:

(1) a method for producing a monoclonal antibody, wherein said method comprises the following steps of:
(a) introducing into a cell,
said cell (i) comprising a rearranged endogenous immunoglobulin heavy chain gene and a rearranged endogenous immunoglobulin light chain gene, and (ii) secreting a monoclonal antibody comprising an immunoglobulin heavy chain polypeptide derived from said rearranged endogenous immunoglobulin heavy chain gene and an immunoglobulin light chain polypeptide derived from said rearranged endogenous immunoglobulin light chain gene,
an exogenous DNA comprising a gene encoding a protein identical to said immunoglobulin heavy chain polypeptide comprised in said cell,
(b) obtaining transformants transformed by the exogenous DNA;
(c) culturing the transformants in a cell culture medium;
(d) obtaining the monoclonal antibody secreted into the cell culture medium;
(2) the method of production according to (1), wherein the gene encoding a protein identical to said immunoglobulin heavy chain polypeptide is a gene comprising a nucleotide sequence identical to the endogenous immunoglobulin heavy chain gene;
(3) the method of production according to (1) or (2), wherein the cells comprise immortalized B cells derived from B cells of a mammal;
(4) the method of production according to (3), wherein the immortalized B cells comprise fused cells obtained by fusing B cells with myeloma cells or recombinant myeloma cells;
(5) the method of production according to (3) or (4), wherein the mammal is a non-human mammal;
(6) the method of production according to (3) or (4), wherein the mammal is a human;
(7) the method of production according to (3) or (4), wherein the mammal is a transgenic non-human mammal that produces a human antibody;
(8) the method of production according to any one of (1) to (4), (6), and (7), wherein the endogenous immunoglobulin heavy chain gene is a human immunoglobulin heavy chain gene;
(9) the method of production according to any one of (1) to (4), (6), and (7), wherein the endogenous immunoglobulin light chain gene is a human immunoglobulin light chain gene;
(10) the method of production according to any one of (1) to (5), wherein the monoclonal antibody is a monoclonal antibody of a non-human mammal;

(11) the method of production according to any one of (1) to (4), (6), and (7), wherein the monoclonal antibody is a human monoclonal antibody;

(12) the method of production according to any one of (1) to (11), wherein the exogenous DNA further comprises a gene-amplification gene;

(13) the method of production according to (12), wherein the gene-amplification gene is dihydrofolate reductase (DHFR) gene; and,

(14) a transformant produced by the method of any one of (1) to (13)

The present invention is illustrated in detail below by revealing the meaning of terms used in the present invention, and its specific embodiments.

In the present invention, "a mammal" means a mammal such as a human, cow, sheep, pig, goat, rabbit, rat, hamster, guinea pig, or mouse, and the following "a transgenic non-human mammal that produces a human antibody" is encompassed therein.

In the present invention, "a non-human mammal" means any animal except humans, and specifically means a mammal such as a cow, sheep, pig, goat, rabbit, rat, hamster, guinea pig, or mouse, and includes the following "a transgenic non-human mammal that produces a human antibody".

In the present invention, "an antigen" means a given substance recognized as non-self by immunocompetent cells in the living body of the above mammals, and encompasses exogenous antigens which are foreign to the living body, and given endogenous substances within the living body with which the living body can produce autoantibodies.

Examples of exogenous antigens are various viruses, bacteria, bacterial toxins, and chemical substances, and in the case of using a specific mammal as a living body, a given substance derived from an individual or an animal species different from the living body (for example, tissues, cells, proteins, and fragments and fluids thereof) are included.

Examples of endogenous substances are, under certain circumstances, various cytokines, growth factors, hormones, cell surface molecules (for example, receptors, channel molecules, signal transduction molecules), and autoreactive lymphocytes that are excessively produced within the living body.

In the present invention, "a monoclonal antibody" means a given monoclonal antibody comprising reactivity to the above antigens.

The "monoclonal antibody" also includes natural monoclonal antibodies prepared by immunizing mammals such as mice, rats, hamsters, guinea pigs, or rabbits with the above-described antigen, a chimeric monoclonal antibody (chimeric antibody) or a humanized antibody (CDR-grafted antibody) produced by recombinant technology, and a human monoclonal antibody (human antibody) obtained by using human antibody-producing transgenic animals and such.

The monoclonal antibody includes those having any one of the isotypes of IgG (IgG1, IgG2, IgG3, and IgG4), IgM, IgA, IgD, IgE, etc. IgG (IgG1, IgG2, IgG3, and IgG4) or IgM is preferable.

"A cell secreting a monoclonal antibody" in the present invention means a given cell comprising a rearranged endogenous immunoglobulin heavy chain gene and a rearranged endogenous immunoglobulin light chain gene, and secretes a monoclonal antibody comprising an immunoglobulin heavy chain polypeptide derived from the endogenous immunoglobulin heavy chain gene and an immunoglobulin light chain polypeptide derived from the endogenous immunoglobulin light chain gene.

Preferably, the cell is a given "monoclonal antibody-producing immortalized B cell" described below, and more preferably, a hybridoma obtained by fusing a monoclonal antibody-producing B cell with, for example, a myeloma cell.

"A monoclonal antibody-producing immortalized B cell" in the present invention means a B cell producing a monoclonal antibody against an antigen produced in the living body of the above mammals by immunizing the living body by the antigen, as well as an immortalized B cell obtained by immortalizing the B cell by a desired method.

This "monoclonal antibody producing B cell" and "monoclonal antibody producing immortalized B cell" can be produced by known methods.

Namely, mammals, preferably, mice, rats, hamsters, guinea pigs, rabbits, cats, dogs, pigs, goats, horses, bovine, or non-human transgenic mammals designed to produce an antibody derived from other animal, for example, human antibody producing transgenic non-human mammals describe below, are immunized, for example, with an antigen mentioned above with Freund's adjuvant, if necessary.

Immunization is done by an injection or implantation into skin, muscle, vein, footpad, or abdomen, once or several times.

Normally, immunization is done once to 4 times roughly every 1 to 14 days after the first immunization. If necessary, a further immunization is conducted 1 or 2 days before the collection of monoclonal antibody producing cells.

B cells, which are antibody-producing cells, are collected from the spleen, lymph node, bone marrow, tonsils, and preferably from the spleen of the above-described immunized mammal by following standard methods.

The antibody-producing immortalized B cells are obtained by fusing these antibody-producing B cells with mammalian (preferably a mammal such as a mouse, rat, Guinea pig, hamster, rabbit, or human, and more preferably a mouse, rat, or human) myeloma cells incapable of producing autoantibodies to immortalize and make them hybridomas using the method of Kohler and Milstein (Nature, Vol. 256, p, 495-497, 1975) or a similar modification method.

For example, mouse-derived myeloma P3/X63-AG8.653 (653, ATCC No. CRL1580), P3/NSI/1-Ag4-1 (NS-1), NSO, P3/X63-Ag8.U1 (P3U1), SP2/0-Ag14 (Sp2/0, Sp2), PAI, F0, or BW5147; rat-derived myeloma 210RCY3-Ag.2.3.; or human-derived myeloma U-266AR1, GM1500-6TG-A1-2, UC729-6, CEM-AGR, D1R11, or CEM-T15 can be used as myeloma used for the cell fusion.

Monoclonal antibody producing hybridoma (monoclonal antibody producing immortalized B cells) prepared as described above, can be screened by cultivating the hybridoma, for example, within microtiter plates, and measuring the reactivity of the culture supernatants in wells in which hybridoma growth is observed towards the immunogen used for the immunization mentioned above, by, for example, an enzyme immunoassay such as RIA and ELISA.

"A human antibody" or "a human immunoglobulin" in the present invention is an immunoglobulin in which all the regions constructing the above immunoglobulin, including the variable region ($V_H$) and the constant region ($C_H$) in the H chain, as well as the variable region ($V_L$) and the constant region ($C_L$) in the L chain, derive from a gene encoding human immunoglobulin. In other words, it means an antibody in which the H chain is derived from a human immunoglobulin heavy chain gene, and the light chain is derived from a human immunoglobulin light chain gene.

Human antibodies can be produced in the same way used to produce monoclonal antibodies as mentioned above, for example, by immunizing a transgenic animal prepared by integrating at least human immunoglobulin gene(s) into the locus of a non-human mammal, such as a mouse, by a well-known method.

For example, a transgenic mouse producing human antibodies is prepared by methods described in published reports; Nature Genetics, Vol. 7, pp. 13-21 (1994); Nature Genetics, Vol. 15, pp. 146-156 (1997); Published Japanese Translation of International Patent Application No. Hei 4-504365; Nikkei Science, June, pp. 40-50 (1995); WO94/25585; Nature, Vol. 368, pp. 856-859 (1994); and Published Japanese Translation of International Patent Application No. Hei 6-500233. The method of the present invention for producing a monoclonal antibody comprises the following steps of:

(a) introducing into a cell,
   said cell (i) comprising a rearranged endogenous immunoglobulin heavy chain gene and a rearranged endogenous immunoglobulin light chain gene, and (ii) secreting a monoclonal antibody comprising an immunoglobulin heavy chain polypeptide derived from said rearranged endogenous immunoglobulin heavy chain gene and an immunoglobulin light chain polypeptide derived from said rearranged endogenous immunoglobulin light chain gene,
   an exogenous DNA comprising a gene encoding a protein identical to said immunoglobulin heavy chain polypeptide comprised in said cell,
(b) obtaining transformants transformed by the exogenous DNA;
(c) culturing the transformants in a cell culture medium;
(d) obtaining the monoclonal antibody secreted into the cell culture medium.

"A gene encoding a protein identical to said immunoglobulin heavy chain polypeptide" means a gene (preferably cDNA) encoding a protein identical to said immunoglobulin heavy chain polypeptide encoded by an endogenous immunoglobulin heavy chain gene comprised in the above cells which produce a monoclonal antibody (preferably antibody-producing B cells or antibody producing immortalized B cells (hybridoma, etc.)). The cDNA can be prepared as follows by using standard methods using known cell technology and gene recombinant technologies.

(1) PolyA $^+$RNA is extracted and purified from hybridoma producing a desired monoclonal antibody by using commercial regents (for example, FastTrack2.0 Kit (INVITROGEN)) according to a standard method. A specific example is as follows:

Frozen hybridoma are lysed in a lysis buffer and solubilized by homogenizing with a commercially available cell lysis reagent (for example, POLYTRON). After incubating at a suitable temperature (for example, about 45° C.), the solubilized materials are mixed with Oligo(dT) cellulose, and shaken gently for a suitable duration (for example, about 1 hour).

Subsequently, the Oligo(dT) cellulose is washed, and then polyA$^+$ RNAs are eluted with an elution buffer. Eluted PolyA$^+$ RNAs are precipitated with ethanol, and then dissolved in a suitable volume of Tris-EDTA buffer. The concentrations of obtained polyA$^+$ RNAs are determined by measuring absorbance at a suitable wave length (for example, 260 nm).

(2) Complementary DNAs are prepared by using the obtained polyA$^+$ RNAs as templates by RACE-PCR using a commercially available reagent (for example, MARATHON cDNA AMPLIFICATION KIT (CLONTECH)) according to the usual procedure ("PCR Method for Gene Amplification: Basic Techniques and Recent Advancement" Kyoritsu Shuppan Co., Ltd., p. 13-15, 1992). Specifically, the method is as follows:

First-strand cDNA synthesis is performed using a suitable volume of purified polyA$^+$ RNA (e.g. about 1 to 5 μg) as the template, and then the second strand is prepared from the first strand. The cDNAs are extracted with phenol/chloroform/isoamyl alcohol, and then chloroform. Then, the cDNAs are precipitated with ethanol, and ligated to an adaptor DNA. PCR is conducted using the obtained DNA diluted to an appropriate concentration (for example, 1/250) as the template and using primers designed based on the nucleotide sequence encoding the amino acid sequence of the constant region in the heavy chain of the monoclonal antibody produced by the hybridoma and primers designed based on the nucleotide sequence of the adapter DNA, using standard methods. The obtained PCR product is fractionated by agarose gel electrophoresis to collect cDNA.

(3) The nucleotide sequence of cDNA encoding the whole or a part of the amino acid sequence of the heavy chain of the obtained monoclonal antibody is determined by using commercial regents (for example, Dye Terminator Cycle Sequence Kit (PE-Applied Biosystems) and the PRISM 377 DNA Sequencer (PE-Applied Biosystems)).

(4) A pair of primer DNA is synthesized based on the nucleotide sequence of cDNA encoding a part of the amino acid sequence of the heavy chain of the monoclonal antibody so as to enable the obtaining of cDNA encoding the full length amino acid sequence of the heavy chain polypeptide by PCR. Then, using the pair of primer DNA, PCR is conducted in the same manner as described above, using the above purified Poly A$^+$RNA as the template to obtain cDNA encoding the full length heavy chain polypeptide.

The method of the present invention for producing a monoclonal antibody comprises: introducing "a gene encoding a protein identical to said immunoglobulin heavy chain polypeptide" described above into cells secreting a monoclonal antibody comprising the immunoglobulin heavy chain polypeptide (preferably a monoclonal antibody-producing hybridoma itself which was used as the source in the preparation of the gene, specifically, synonymous with the above monoclonal antibody-producing B cells or immortalized B cells) using the genetic engineering technology according to standard methods; screening and isolating transformant cells transformed by the gene; and purifying the monoclonal antibody from the cell culture solution by culturing the transformants to obtain the monoclonal antibody.

The gene (for example, cDNA) is introduced into the cells by preparing a plasmid vector-incorporated expression vector so that the gene can be expressed in host cells by following standard methods, and transforming host cells by the expression vector.

cDNA can be inserted into a plasmid by, for example, the method of Maniatis et al. (Molecular Cloning, A Laboratory Manual, second edition, Cold Spring Harbor Laboratory, p. 1.53, 1989).

Examples of methods for introducing a plasmid into a host are, the calcium chloride method, calcium chloride/rubidium chloride method, and electroporation method, described in Molecular Cloning, A Laboratory Manual (second edition, Cold Spring Harbor Laboratory, Vol. 1.74 (1989)).

Any vector can be used in the present invention, as long as it can maintain replication and self-multiply in host cells (preferably eukaryotic cells), and includes, plasmid vectors and phage vectors.

Specific examples of plasmids are pLS407, pBR322, pBR325, pUC12, pUC13, pUC19, pSH19, pSH15, pUB110, pTP5, pC194, pcD2, pBSV, CMD, pSV2, as well as PMAL C2, pEF-BOS (Nucleic Acid Research, Vol. 18, p. 5322, 1990) and pME18S (Experimental Medicine, Supplement "Genetic engineering handbook" 1992 etc.).

Examples of phages are, bacteriophages such as λ phages, and animal and insect viruses (pVL1393, INVITROGEN) such as retroviruses, vaccinia viruses, and nuclear polyhedrosis viruses. When bacteria, particularly *E. coli* are used as host cells, an expression vector generally comprises at least a promoter/operator region, an initiation codon, and the gene encoding the immunoglobulin heavy chain (IgH) as mentioned above, termination codon, terminator region, and replicon.

When yeasts, animal cells, or insect cells are used as hosts, an expression vector preferably comprises at least a promoter, an initiation codon, the gene encoding the immunoglobulin heavy chain (IgH) as mentioned above, and a termination codon.

The expression vector may also comprise DNA encoding a signal peptide, enhancer sequence, 5' and 3' untranslated regions of the gene encoding the immunoglobulin heavy chain (IgH) as mentioned above, splicing junctions, polyadenylation site, selectable marker region, and replicon.

Moreover, the expression vector may also contain, if required, a gene for gene amplification that is usually used.

Examples of promoters for expressing the above gene encoding a desired immunoglobulin heavy chain (IgH chain) in eukaryotic cells such as mammalian cells are, β actin promoter derived from chicken, a SV40-derived promoter, a retrovirus promoter, and a heat shock promoter. Preferable are, the β actin promoter derived from chicken, the SV40-derived promoter, and the retrovirus promoter, but the promoters are not specifically limited thereto.

The use of an enhancer is also an effective method for expression, the CMV enhancer being a preferable example.

A promoter/operator region to express the gene encoding the desired immunoglobulin heavy chain (IgH) mentioned above in bacteria comprises a promoter, an operator, and a Shine-Dalgarno (SD) sequence (for example, AAGG). For example, when the host is *Escherichia*, it preferably comprises Trp promoter, lac promoter, recA promoter, XPL promoter, lpp promoter, tac promoter, or the like.

Examples of a promoter to express the gene encoding the immunoglobulin heavy chain (IgH) as mentioned above in yeast are PH05 promoter, PGK promoter, GAP promoter, ADH promoter, and so on. When the host is *Bacillus*, examples thereof are SL01 promoter, SP02 promoter, penP promoter, and so on.

A preferable initiation codon is, for example, a methionine codon (ATG).

Commonly used termination codons (for example, TAG, TGA, TAA) are examples of termination codons. Usually, natural or synthetic terminators are used as terminator regions.

A replicon means a DNA capable of replicating the whole DNA sequence within host cells, and includes a natural plasmid, an artificially modified plasmid (DNA fragment prepared from a natural plasmid), a synthetic plasmid, and so on. Examples of preferable plasmids are pBR322 or its artificial derivatives (DNA fragment obtained by treating pBR322 with appropriate restriction enzymes) for *E. coli*, yeast 2μ plasmid or yeast chromosomal DNA for yeast, and pRSVneo ATCC 37198, pSV2dhfrATCC 37145, pdBPV-MMTneo ATCC 37224, pSV2neo ATCC 37149, and such, for mammalian cells.

An enhancer sequence, polyadenylation site, and splicing junction usually used in the art, such as those derived from SV40 can also be used.

The above expression vector can be prepared by connecting, for example, the above promoter, an initiation codon, the above gene encoding IgH chain, and/or a terminator region in a continuous, circular manner in a unit capable of replication. When doing so, an appropriate DNA fragment (for example, a linker, another restriction enzyme cleavage site) made using standard methods, for example, digestion with restriction enzymes, and ligation using T4 DNA ligase, can be used, if desired.

Host cells transformed by the above expression vector, specifically transformants, can be selected by inserting a desired selective marker (for example, a drug resistance gene) into the expression vector, and culturing the transformants in the presence of the drug.

A selective marker usually employed can be used according to the usual method. Examples thereof are genes resistant to antibiotics, such as tetracycline, ampicillin, or kanamycin.

The above method of the present invention for producing a monoclonal antibody further includes, an embodiment for improving production efficiency of a desired monoclonal antibody by the transformants by increasing the copy number of the gene encoding the heavy chain polypeptide by inserting a gene-amplification gene together with the gene encoding the heavy chain polypeptide of the above desired monoclonal antibody.

Examples of genes for gene amplification in present invention are dihydrofolate reductase (DHFR) gene, thymidine kinase gene, neomycin resistance gene, glutamate synthase (GS) gene, adenosine deaminase gene, ornithine decarboxylase gene, hygromycin-B-phophotransferase gene, aspartate transcarbamylase gene, etc. Preferable is the DHFR gene or the GS gene.

In the method of the present invention for producing a monoclonal antibody, the cell (a host) transformed by the above "gene encoding a protein identical to said immunoglobulin heavy chain polypeptide" is any cell as long as it is a cell secreting a monoclonal antibody comprising the immunoglobulin heavy chain polypeptide, and preferably in particular, the monoclonal antibody-producing hybridoma used as the source to prepare the gene itself (specifically, synonymous with the above monoclonal antibody-producing B cell or immortalized B cell).

Examples of host cells besides hybridoma include various cells, such as natural cells or artificially established recombinants (for example, bacteria (*Escherichia, Bacillus*), yeast (*Saccharomyces, Pichia*)), animal cells, or insect cells as long as the cells produce the desired monoclonal antibody.

As long as the cells produce the desired monoclonal antibody, they can be from any source such as *E. coli* (for example, DH 5α, TB1, HB101), mice (for example, COP, L, C127, Sp2/0, NS-1, or NIH3T3), rats (PC12, PC12h), hamsters (for example, BHK and CHO), monkeys (for example, COS1, COS3, COS7, CV1, and Velo), and humans (Hela, cells derived from diploid fibroblasts, myeloma cells, and HepG2).

The introduction (transformation (transfection)) of expression vector having the gene encoding the heavy chain of the above-mentioned desired immunoglobulin into host cells can be conducted by a conventionally known method.

For example, the transformation can be conducted by the following methods: for example, the method of Graham (Virology, Vol. 52, p. 456 1973) in the case of animal cells; the method of Cohen et al. (Proc. Natl. Acad. Sci. USA., Vol. 69, p. 2110, 1972), the protoplast method (Mol. Gen. Genet., Vol.

168 p 111, 1979), the competent method (J. Mol. Biol., Vol. 56, p 209, 1971) in the case of bacteria (for example, *E. coli, Bacillus subtilis*); the method of Hinnen et al. (Proc. Natl. Acad. Sci. USA., Vol. 75, p. 1927, 1978) or the lithium method (J. Bacteriol., Vol. 153, p. 163, 1983) in the case of *Saccharomyces cerevisiae*; and the method of Summers et al. (Mol. Cell. Biol., Vol. 3. p. 2156-2165, 1983) in the case of insect cells.

The "transformants" used in the above-mentioned method of the present invention to produce a monoclonal antibody, and which have been transformed by the gene encoding the above desired immunoglobulin heavy chain, can be cultured by standard methods as described below. The desired monoclonal antibody can be obtained from the cell culture solution.

When cells transformed by the gene encoding the heavy chain of the desired immunoglobulin is monoclonal antibody producing-hybridoma used as the source for preparing the gene itself (synonymous with the above monoclonal antibody producing B cells or immortalized B cells), specifically, when the obtained trans formants are recombinant hybridoma, the hybridoma can be cultured in the same manner as in the common method for culturing hybridoma.

Specifically, the recombinant hybridoma are cultured in vitro or in vivo such as in the ascites of mice, rats, guinea pigs, hamsters, or rabbits, preferably mice or rats, more preferably mice, and the antibodies are isolated from the resulting the culture supernatant or ascites of the mammal.

Cultivating the cells in vitro can be performed using known nutrient media, or any nutrient media derived from known basal media used for growing, maintaining, and storing the hybridomas, and producing monoclonal antibodies in the culture supernatant. Various culture media are used depending on the features of cells cultured, on the aim of the experiment, and on the culture method, and such various conditions.

Examples of basal media are low calcium concentration media such as Ham'F12 medium, MCDB153 medium, or low calcium concentration MEM medium, and high calcium concentration media such as MCDB104 medium, MEM medium, D-MEM medium, RPMI1640 medium, ASF104 medium, or RD medium. The basal media can contain, for example, sera, hormones, cytokines, and/or various inorganic or organic substances depending on the objective.

Isolation and purification of monoclonal antibodies from the recombinant hybridoma can be done by, for example, subjecting the culture supernatant or ascites mentioned above to saturated ammonium sulfate precipitation, euglobulin precipitation method, caproic acid method, caprylic acid method, ion exchange chromatography (DEAE or DE52), affinity chromatography using anti-immunoglobulin column or protein A column.

On the other hand, when cells to be transformed by the gene encoding the heavy chain of the desired immunoglobulin are host cells generally used for producing the above recombinant protein, such as CHO cells, the cells can be cultured in the same manner as in the general method for producing a recombinant protein.

Specifically, monoclonal antibodies can be produced by culturing the recombinant cells in a nutrient medium.

The nutrient media preferably comprise a carbon source, inorganic nitrogen source, or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meet extract, soy bean cake, and potato extract. If desired, the media may comprise other nutrients (for example, an inorganic salt (for example, calcium chloride, sodium dihydrogenphosphate, and magnesium chloride), vitamins, and antibiotics (for example, tetracycline, neomycin, ampicillin, kanamycin, and so on).

Cultivation is performed by a method known in the art. Cultivation conditions such as temperature, pH of the media, and cultivation time are selected appropriately so that the monoclonal antibody of the present invention is produced in large quantities from the transformed cells.

Specific media and cultivation conditions used depending on host cells are illustrated below, but are not limited thereto.

When the hosts are bacteria, actinomycetes, yeasts, filamentous fungi, for example, liquid media comprising a nutrient source mentioned above appropriate. Media with a pH of 5 to 8 are preferably used.

When the host is *E. coli*, examples of preferable media are LB media, M9 media (Miller et al. Exp. Mol. Genet., Cold Spring Harbor Laboratory, p. 431 (1972)), and soon. Using these media, cultivation can be performed usually at 14 to 43° C. for about 3 to 24 hours with aeration and stirring, if necessary.

When the host is *Bacillus*, cultivation can be done usually at 30 to 40° C. for about 16 to 96 hours with aeration and stirring, if necessary.

When the host is yeast, an example of media is the Burkholder minimal media (Bostian, Proc. Natl. Acad. Sci. USA, Vol. 77, p. 4505 (1980)). The pH of the media is preferably 5 to 8. Cultivation can be performed usually at about 20 to 35° C. for about 14 to 144 hours with aeration and stirring, if necessary.

When the host is an animal cell, examples of media are MEM media containing about 5 to 20% fetal bovine serum (Science, Vol. 122, p. 501 (1952)), DMEM media (Virology, Vol. 8, p. 396 (1959)), RPMI1640 media (J. Am. Med. Assoc., Vol. 199, p. 519 (1967)), 199 media (Proc. Soc. Exp. Biol. Med., Vol. 73, p. 1 (1950)), and so on. The pH of the media is preferably about 6 to 8. Cultivation can be performed usually at about 30 to 40° C. for about 15 to 72 hours with aeration and stirring, if necessary.

When the host is an insect cell, an example of media is Grace's media containing fetal bovine serum (Proc. Natl. Acad. Sci. USA, Vol. 82, p. 8404 (1985)). The pH thereof is preferably about 5 to 8. Cultivation can be performed usually at about 20 to 40° C. for 15 to 100 hours with aeration and stirring, if necessary.

The desired monoclonal antibody of the present invention can be obtained by using a common method for purifying it from the culture supernatant of recombinants cultured in the above manner.

Figure 1:
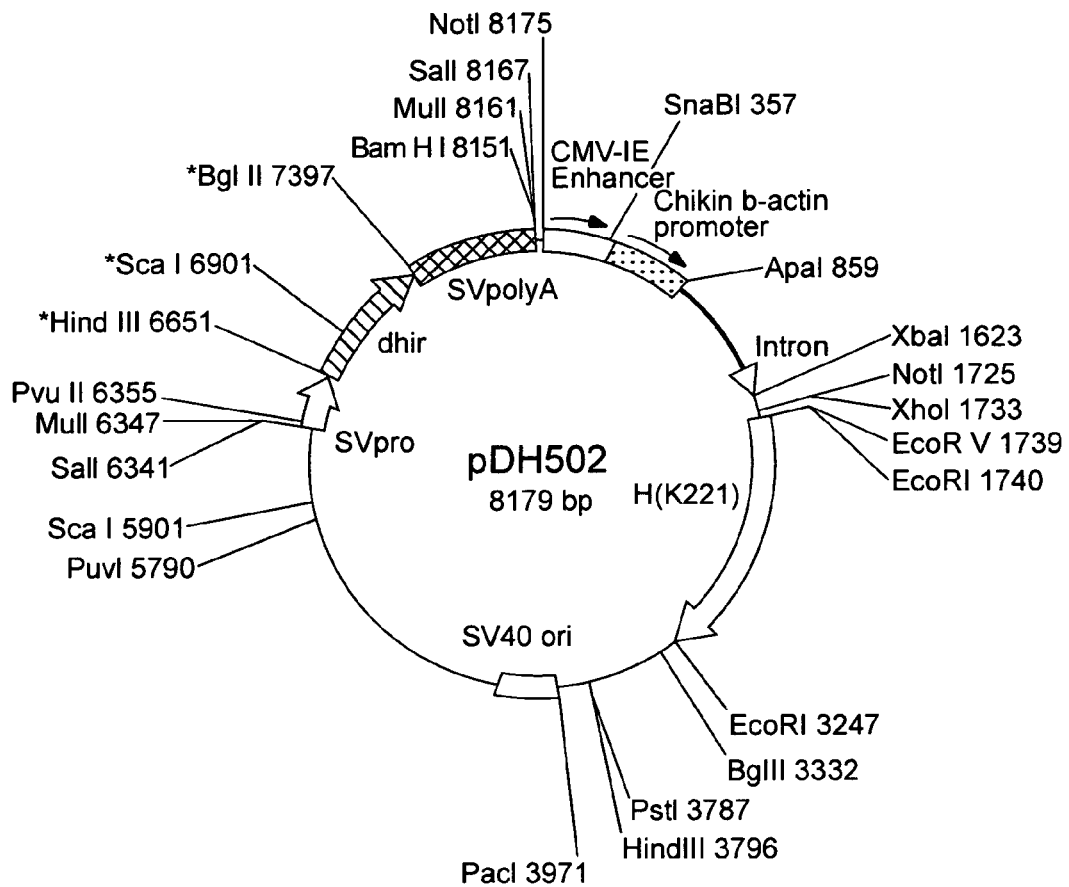
FIG. 1 schematically shows the structure and restriction enzyme map of the expression vector pDH502.

The vertical axis shows the amount of monoclonal antibody produced and the horizontal axis shows each type of recombinant hybridoma clones in each well of the microtiter plate.

BEST MODE FOR CARRYING OUT THE INVENTION

The present inventions are illustrated in detail by the following Examples, but they are not to be construed as being limited to those embodiments.

Example 1

Preparation of Monoclonal Antibody-Producing Hybridoma

A previously reported hybridoma producing the human monoclonal antibody against human IL-8 was used in the following experiments (Nature genetics Vol. 15, p 146-156, 1997, and WO96/33735).

The hybridoma was produced as follows:

A previously reported transgenic mouse producing human IgG$_2$/κ monoclonal antibody, which was prepared by inactivating each of the endogenous locus for mouse heavy and light chain and inserting DNA comprising each locus for heavy (Cμ and Cγ$_2$) and light chain (κ) of human immunoglobulin into mouse endogenous genome, was used as the animal to be immunized (Nature Genetics, Vol. 15, p. 146-156, 1997; Nature Genetics, Vol. 7, p. 13-21, 1994; Published Japanese Translation of International Patent Application No. Hei 4-504365; WO94/25585; Nikkei Science, Issue of June, p. 40-50, 1995; Nature, Vol. 368, p. 856-859, 1994; and Published Japanese Translation of International Patent Application No. Hei 6-500233).

The human IgG$_2$/κ antibody-producing transgenic mouse (8 to 10-week old) was first immunized by intraperitoneally administering recombinant human IL-8 (25 μg) with Freund's complete adjuvant. Additional immunizations (3 times) with IL-8 and Freund's incomplete adjuvant were conducted every 2 weeks after the first immunization and the final immunization was conducted 4 days prior to the following cell fusion.

After the final immunization, lymphocytes (including antibody-producing B lymphocytes) were harvested by collecting the spleen and lymph nodes of the immunized mouse. The antibody-producing lymphocytes were fused with mouse myeloma cells (NSO-bs12 cell line) that do not produce any autoantibodies by following the standard method. Hybridoma cells obtained by cell fusion were selected by the HAT selection method according to the standard method.

The reactivity against human IL-8 of the human monoclonal antibody produced by the hybridoma obtained was assayed by ELISA according to the standard method, and multiple hybridomas producing anti-human IL-8 human monoclonal antibody were obtained. Each hybridoma was frozen and stored.

Example 2

Isolation of Endogenous IgH Gene from Monoclonal Antibody-Producing Hybridoma Frozen cells of anti-human IL-8 human IgG$_2$/κ monoclonal antibody-producing hybridoma (clone: K2.2.1) prepared in the above manner were dissolved in a lysis buffer and disrupted by POLYTRON and solubilized.

PolyA$^+$ RNA was extracted and purified from the solubilized cell mixture using a commercial RNA extraction kit (Fast Track 2.0 Kit (INVITRIGEN)).

The solubilized cell mixture was incubated at 45° C., Oligo (dT) cellulose was added thereto, and gently shaken for about 1 hr. Oligo (dT) cellulose was washed and PolyA$^+$ RNA was eluted by the elution buffer. The eluted PolyA$^+$ RNA was precipitated with ethanol and dissolved in Tris-EDTA buffer. The concentration of the obtained PolyA$^+$ RNA was determined by measuring absorbance at the wavelength of 260 nm.

According to the standard manner, cDNA was synthesized by conducting RACE-PCR using the obtained PolyA$^+$ RNA as the template and the commercial Marathon cDNA Amplification Kit (CLONTECH) ("Gene amplification PCR method, basic and new application" 1992, the second print, Kyoritsu Shuppan, p. 13-15). Specifically, 1st and 2nd strand cDNA were synthesized in succession using PolyA$^+$ RNA (1 to 5 μg) purified from the hybridoma as a template. The cDNA was extracted by using phenol/chloroform/isoamino alcohol and chloroform, once each. cDNA was precipitated with ethanol, and ligated to the adapter DNA accompanying the kit.

The cDNA encoding a part of an endogenous immunoglobulin heavy chain polypeptide was prepared by 5'RACE-PCR using the dilute PCR product so obtained as the template and synthetic primers, according to the standard method. The PCR was conducted by using primer HG2-3-437 designed based on the nucleotide sequence encoding the amino acid sequence of immunoglobulin heavy chain constant region (SEQ ID NO: 3) and a primer designed based on the nucleotide sequence of the adapter DNA.

Each PCR product was fractionated by agarose-gel electrophoresis, and the DNAs of interest were recovered therefrom. The nucleotide sequences of the respective cDNAs so obtained were determined by using a commercially available reagent, DYE TERMINATOR CYCLE SEQUENCING FS KIT (PE-Applied Biosystems) and a PRISM377 DNA Sequencer (PE-Applied Biosystems). Sequencing Primers used in the sequence determination were the same as those used in the above PCR amplification.

Based on the nucleotide sequence so determined (including a nucleotide sequence flanking the translation initiation point) of cDNA encoding a part of the heavy chain polypeptide of the immunoglobulin, the pair of primers VH4-21 (SEQ ID NO: 4) and CG2-1 (SEQ ID NO: 5) was synthesized. Using this pair of primers, PCR was conducted in the same manner as the above. The nucleotide sequence of cDNA obtained from the obtained PCR product was determined in the same manner as the above, and the cDNA encoding the full length heavy chain polypeptide (IgH) of anti-human IL-8 human monoclonal antibody produced by the hybridoma K2.2.1 (Nucleotide Sequence: SEQ ID NO: 1 and amino acid sequence: SEQ ID NO: 2) was obtained.

Example 3

Introduction of IgH cDNA into Hybridoma K.2.2.1 and Preparation of the Monoclonal Antibody by Recombinant Hybridoma The cDNA encoding the full length heavy chain for anti-human IL-8 human monoclonal antibody secreted by the hybridoma K.2.2.1 obtained above (SEQ ID NO: 1) was inserted into an EcoRI restriction site of plasmid pLS407 comprising CMV enhancer/chicken β actin promoter and DHFR gene and ligated to prepare the expression vector pDH502 according to the standard method (FIG. 1).

As the DHFR gene works as both a marker gene and a gene-amplification gene, when this gene is present, the selection of transformants by the expression vector can be done by culturing the cells in the presence of methotrexate (MTX).

The IgH gene expression vector pDH502 was introduced into hybridoma K. 2.2.1 by electroporation. The hybridoma was cultured in a selection medium (IMDM (JRH BIOSCIENCE) containing 10% FBS and 300 mM MTX), and about one hundred grown transformants (recombinant hybridoma) were selected. Each selected recombinant hybridoma was cultured in a 96-well microplate.

The amount of human monoclonal antibody (IgG$_2$) produced in the culture supernatant of each well in which the each of the transformants (recombinant hybridoma) were cultured, was measured by the sandwich ELISA according to the standard method. Anti-human IgG (Fc) (Organon Teknika) was used as the solid antibody (first antibody) and anti-human Igκ antibody labeled with horseradish peroxidase (HRP) (PROTOS IMMUNORESEARCH) was used as the detection antibody (second antibody). As a control sample, human IgG/κ (The Binding Site) was used.

Figure 2:
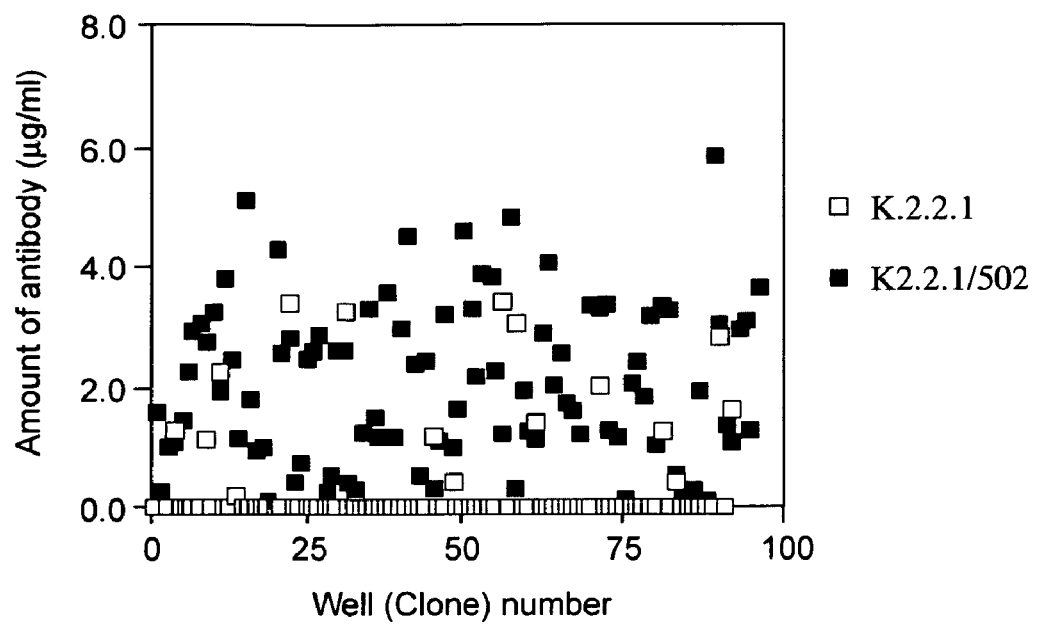
FIG. 2 shows the amount of anti-human IL-8 monoclonal antibody produced by the recombinant hybridoma.

FIG. 2 shows the results.

Namely, it was observed that the amount of monoclonal antibody produced was significantly increased in most recombinant hybridoma clones, while the amount of production in most K2.2.1 clones (the parental hybridoma) was extremely low.

Table 1 shows the amount of monoclonal antibody produced by some recombinant hybridoma clones.

TABLE 1

Antibody Productivity in Recombinant Hybridoma

| Clone No. | Concentration of human IgG$_2$ (µg/ml) |
|---|---|
| 12* | 10.3 |
| 15* | 37.3 |
| 20 | 5.6 |
| 41* | 10.0 |
| 50 | 1.7 |
| 53 | 0.34 |
| 54 | 3.4 |
| 57 | 5.5 |
| 63 | 0.49 |
| 89* | 7.0 |
| 96 | 4.8 |

*Sub-cloning and MTX selection were conducted afterwards.

Sub-cloned recombinant hybridomas (clone Nos: 12-6, 15-4, 15-12, 41-2, and 89-5) were obtained by sub-cloning those recombinant hybridoma clones that produced a highly concentrated monoclonal antibody (clone Nos: 12, 15, 41, and 89) using the limiting dilution method. The amount of monoclonal antibody produced by each sub-cloned recombinant hybridoma was measured by an ELISA similar to the above. Table 2 shows the results (upper section).

TABLE 2

| Clone No. | Concentration of human IgG$_2$ (µg/ml) | Number of cells (cells/ml) | Cultivation period (days) | Productivity (pg/cell/day) |
|---|---|---|---|---|
| sub-cloned | | | | |
| 12-6 | 18.2 | 3.20E+0.5 | 3 | 19 |
| 15-4 | 95.3 | 3.00E+0.5 | 5 | 64 |
| 15-12 | 66.9 | 3.20E+0.5 | 5 | 42 |
| 41-2 | 24.5 | 3.35E+0.5 | 6 | 12 |
| 89-5 | 15.9 | 3.40E+0.5 | 3 | 16 |
| MTX selection | | | | |
| 12-5µ-96-8 | 23.6 | 5.25E+0.5 | 4 | 11 |
| 15-1µ-82-1 | 107.0 | 7.30E+0.5 | 4 | 37 |
| 15-1µ-87-4 | 67.1 | 5.55E+0.5 | 4 | 30 |
| 41-2µ-75-4 | 19.6 | 8.20E+0.5 | 4 | 6 |
| 89-2µ-2-5 | 11.9 | 6.15E+0.5 | 4 | 5 |
| 89-5µ-33-12 | 11.8 | 6.65E+0.5 | 4 | 4 |

As a result, the amount of monoclonal antibody produced by each sub-cloned recombinant hybridoma was significantly higher than that in the parental recombinant hybridoma. For example, the amount of antibody produced by the parental recombinant hybridoma (No. 15) was about 37.3 µg/ml, while the amount produced by the recombinant hybridoma sub-cloned from the parental line (No. 15-4) was increased to about 95.3 µg/ml.

Example 4

Preparation of the Monoclonal Antibody from Gene-Amplified Recombinant Hybridoma The effect of the amplification of IgH gene by DHFR gene on the production efficiency of the monoclonal antibody was studied.

Each sub-cloned recombinant hybridoma prepared above (clone Nos. 12-6, 15-4, 15-12, 41-2, and 89-5) was further cultured in a nutrient medium containing 1, 2, or 5 µM methotrexate (MTX), and MTX-resistant cells were selected.

From each sub-cloned recombinant hybridoma, the following MTX-resistant cell lines were obtained.

<clone No. 12-6> Clone No. 12-5 µ-96-8
<clone No. 15-4> Clone No. 15-1 µ-82-1
<clone No. 15-12> Clone No. 15-1 µ-87-4
<clone No. 41-2> Clone No. 41-2 µ-75-4
<clone No. 89-5> Clone No. 89-2 µ-2-5, and 89-2 µ-33-12

The amount of monoclonal antibody produced by each MTX-resistant recombinant hybridoma clone was measured by a sandwich ELISA similar to the above. The above Table 2 shows the result (lower section).

Namely, the production efficiency of monoclonal antibody per cell for each recombinant hybridoma selected by MTX was low compared to that before the MTX selection (before gene amplification by DHFR), however, when considering that only an extremely small amount of monoclonal antibody was produced by wild type parental hybridoma K2.2.1 (FIG. 2), the production efficiency of monoclonal antibody in the recombinant hybridoma selected by MTX was significantly increased in comparison to that in the wild type parental hybridoma.

INDUSTRIAL APPLICABILITY

As described above, the use of the method in the present invention enables one to significantly and conveniently increase monoclonal antibody production by monoclonal antibody-producing cells in the production of monoclonal antibodies useful as drugs.

In particular, when the production efficiency of a monoclonal antibody in monoclonal antibody-producing immortalized B cells (hybridoma) that are generally used for the production of monoclonal antibodies is low due to the instability of endogenous IgH gene expression or low expression thereof, the amount of monoclonal antibody secreted by of the parental hybridoma can be significantly increased by using the method of the present invention.

Therefore, the method of the present invention for producing a monoclonal antibody, and monoclonal antibody-producing transformants (recombinant cells) obtained by the method are extremely useful means in the production of antibody drugs.

The invention claimed is:

1. A method of producing a monoclonal antibody, comprising the steps of:
   fusing a B cell of a transgenic mouse which expresses human antibodies with a myeloma cell line incapable of producing antibodies to obtain a hybridoma, wherein the hybridoma comprises a rearranged immunoglobulin heavy chain nucleotide sequence which expresses a heavy chain polypeptide, and a rearranged immunoglobulin light chain nucleotide sequence which expresses a light chain polypeptide;
   introducing into the hybridoma an exogenous nucleotide sequence which encodes a heavy chain polypeptide identical to the heavy chain polypeptide expressed by the rearranged immunoglobulin heavy chain nucleotide sequence to thereby obtain a transformant hybridoma transformed with the exogenous nucleotide sequence wherein the exogenous nucleotide sequence does not encode the light chain polypeptide;
   culturing the transformant in a cell culture medium; and
   obtaining a monoclonal antibody produced by the transformant.

2. The method of claim 1, wherein the myeloma cell line is a recombinant myeloma cell line.

3. The method of claim 1, wherein the exogenous sequence further comprises a gene-amplification gene.

4. The method of claim 3, wherein the gene-amplification gene is dihydrofolate reductase (DHFR) gene.

5. A transformant produced by a method comprising the steps of:
   fusing a B cell of a transgenic mouse which expresses human antibodies with a myeloma cell line incapable of producing antibodies to obtain a hybridoma, wherein the hybridoma comprises a rearranged immunoglobulin heavy chain nucleotide sequence which expresses a heavy chain polypeptide, and a rearranged immunoglobulin light chain nucleotide sequence which expresses a light chain polypeptide;
   introducing into the hybridoma an exogenous nucleotide sequence which encodes a heavy chain polypeptide identical to the heavy chain polypeptide expressed by the endogenous immunoglobulin heavy chain to thereby obtain a transformant hybridoma transformed with the exogenous nucleotide sequence wherein the exogenous nucleotide sequence does not encode the light chain polypeptide;
   culturing the transformant in a cell culture medium; and
   obtaining a transformant.

* * * * *

SEQUENCE LISTING

<160> NUMBER OF SEQ ID NOS: 5

<210> SEQ ID NO 1
<211> LENGTH: 1507
<212> TYPE: DNA
<213> ORGANISM: Homo sapiens
<220> FEATURE:
<221> NAME/KEY: CDS
<222> LOCATION: (12)..(1400)

<400> SEQUENCE: 1

```
gaattcggct t atg aaa cac ctg tgg ttc ttc ctc ctc ctg gtg gca gct        50
            Met Lys His Leu Trp Phe Phe Leu Leu Leu Val Ala Ala
            1               5                   10 ccc aga tgg gtc ctg tcc cag gtt cag cta cag cag tgg ggc gca gga        98
Pro Arg Trp Val Leu Ser Gln Val Gln Leu Gln Gln Trp Gly Ala Gly
    15                  20                  25 ctg ttg aag cct tcg gag acc ctg tcc ctc acc tgc gct gtc tat ggt       146
Leu Leu Lys Pro Ser Glu Thr Leu Ser Leu Thr Cys Ala Val Tyr Gly
30                  35                  40                  45 ggg tcc ttc agt ggt tac tac tgg acc tgg atc cgc cag ccc cca ggg       194
Gly Ser Phe Ser Gly Tyr Tyr Trp Thr Trp Ile Arg Gln Pro Pro Gly
                50                  55                  60 aag ggg ctg gag tgg att ggg gaa atc att cat cat gga aac acc aac       242
Lys Gly Leu Glu Trp Ile Gly Glu Ile Ile His His Gly Asn Thr Asn
            65                  70                  75 tac aac ccg tcc ctc aag agt cga gtc tcc ata tca gtt gac acg tcc       290
Tyr Asn Pro Ser Leu Lys Ser Arg Val Ser Ile Ser Val Asp Thr Ser
        80                  85                  90 aag aac cag ttc tcc ctg aca ctg agc tct gtg acc gcc gcg gac acg       338
Lys Asn Gln Phe Ser Leu Thr Leu Ser Ser Val Thr Ala Ala Asp Thr
    95                  100                 105 gct gtg tat tac tgt gcg aga ggg gga gca gtg gct gcg ttt gac tac       386
Ala Val Tyr Tyr Cys Ala Arg Gly Gly Ala Val Ala Ala Phe Asp Tyr
110                 115                 120                 125 tgg ggc cag gga acc ctg gtc acc gtc tcc tca gcc tcc acc aag ggc       434
Trp Gly Gln Gly Thr Leu Val Thr Val Ser Ser Ala Ser Thr Lys Gly
                130                 135                 140 cca tcg gtc ttc ccc ctg gcg ccc tgc tcc agg agc acc tcc gag agc       482
Pro Ser Val Phe Pro Leu Ala Pro Cys Ser Arg Ser Thr Ser Glu Ser
            145                 150                 155 aca gcg gcc ctg ggc tgc ctg gtc aag gac tac ttc ccc gaa ccg gtg       530
Thr Ala Ala Leu Gly Cys Leu Val Lys Asp Tyr Phe Pro Glu Pro Val
        160                 165                 170 acg gtg tcg tgg aac tca ggc gct ctg acc agc ggc gtg cac acc ttc       578
Thr Val Ser Trp Asn Ser Gly Ala Leu Thr Ser Gly Val His Thr Phe
    175                 180                 185 cca gct gtc cta cag tcc tca gga ctc tac tcc ctc agc agc gtg gtg       626
Pro Ala Val Leu Gln Ser Ser Gly Leu Tyr Ser Leu Ser Ser Val Val
190                 195                 200                 205 acc gtg ccc tcc agc aac ttc ggc acc cag acc tac acc tgc aac gta       674
Thr Val Pro Ser Ser Asn Phe Gly Thr Gln Thr Tyr Thr Cys Asn Val
                210                 215                 220 gat cac aag ccc agc aac acc aag gtg gac aag aca gtt gag cgc aaa       722
Asp His Lys Pro Ser Asn Thr Lys Val Asp Lys Thr Val Glu Arg Lys
            225                 230                 235 tgt tgt gtc gag tgc cca ccg tgc cca gca cca cct gtg gca gga ccg       770
Cys Cys Val Glu Cys Pro Pro Cys Pro Ala Pro Pro Val Ala Gly Pro
        240                 245                 250 tca gtc ttc ctc ttc ccc cca aaa ccc aag gac acc ctc atg atc tcc       818
```

-continued

```
Ser Val Phe Leu Phe Pro Pro Lys Pro Lys Asp Thr Leu Met Ile Ser
        255                 260                 265 cgg acc cct gag gtc acg tgc gtg gtg gtg gac gtg agc cac gaa gac      866
Arg Thr Pro Glu Val Thr Cys Val Val Val Asp Val Ser His Glu Asp
270                 275                 280                 285 ccc gag gtc cag ttc aac tgg tac gtg gac ggc gtg gag gtg cat aat      914
Pro Glu Val Gln Phe Asn Trp Tyr Val Asp Gly Val Glu Val His Asn
                290                 295                 300 gcc aag aca aag cca cgg gag gag cag ttc aac agc acg ttc cgt gtg      962
Ala Lys Thr Lys Pro Arg Glu Glu Gln Phe Asn Ser Thr Phe Arg Val
        305                 310                 315 gtc agc gtc ctc acc gtt gtg cac cag gac tgg ctg aac ggc aag gag     1010
Val Ser Val Leu Thr Val Val His Gln Asp Trp Leu Asn Gly Lys Glu
320                 325                 330 tac aag tgc aag gtc tcc aac aaa ggc ctc cca gcc ccc atc gag aaa     1058
Tyr Lys Cys Lys Val Ser Asn Lys Gly Leu Pro Ala Pro Ile Glu Lys
                335                 340                 345 acc atc tcc aaa acc aaa ggg cag ccc cga gaa cca cag gtg tac acc     1106
Thr Ile Ser Lys Thr Lys Gly Gln Pro Arg Glu Pro Gln Val Tyr Thr
        350                 355                 360                 365 ctg ccc cca tcc cgg gag gag atg acc aag aac cag gtc agc ctg acc     1154
Leu Pro Pro Ser Arg Glu Glu Met Thr Lys Asn Gln Val Ser Leu Thr
                370                 375                 380 tgc ctg gtc aaa ggc ttc tac ccc agc gac atc gcc gtg gag tgg gag     1202
Cys Leu Val Lys Gly Phe Tyr Pro Ser Asp Ile Ala Val Glu Trp Glu
                385                 390                 395 agc aat ggg cag ccg gag aac aac tac aag acc aca cct ccc atg ctg     1250
Ser Asn Gly Gln Pro Glu Asn Asn Tyr Lys Thr Thr Pro Pro Met Leu
        400                 405                 410 gac tcc gac ggc tcc ttc ttc ctc tac agc aag ctc acc gtg gac aag     1298
Asp Ser Asp Gly Ser Phe Phe Leu Tyr Ser Lys Leu Thr Val Asp Lys
415                 420                 425 agc agg tgg cag cag ggg aac gtc ttc tca tgc tcc gtg atg cat gag     1346
Ser Arg Trp Gln Gln Gly Asn Val Phe Ser Cys Ser Val Met His Glu
430                 435                 440                 445 gct ctg cac aac cac tac acg cag aag agc ctc tcc ctg tct ccg ggt     1394
Ala Leu His Asn His Tyr Thr Gln Lys Ser Leu Ser Leu Ser Pro Gly
                450                 455                 460 aaa tga gtgccacggc cggcaagccc ccgctcccca ggctctcggg gtcgcgtgag     1450
Lys gatgcttggc acgtaccccg tgtacatact tcccaggcac ccagcaaagc cgaattc       1507

<210> SEQ ID NO 2
<211> LENGTH: 462
<212> TYPE: PRT
<213> ORGANISM: Homo sapiens

<400> SEQUENCE: 2

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
        35                  40                  45

Ser Gly Tyr Tyr Trp Thr Trp Ile Arg Gln Pro Pro Gly Lys Gly Leu
    50                  55                  60

Glu Trp Ile Gly Glu Ile Ile His His Gly Asn Thr Asn Tyr Asn Pro
65                  70                  75                  80

Ser Leu Lys Ser Arg Val Ser Ile Ser Val Asp Thr Ser Lys Asn Gln
```

```
                   85                  90                  95
Phe Ser Leu Thr Leu Ser Ser Val Thr Ala Ala Asp Thr Ala Val Tyr
               100                 105                 110
Tyr Cys Ala Arg Gly Gly Ala Val Ala Ala Phe Asp Tyr Trp Gly Gln
               115                 120                 125
Gly Thr Leu Val Thr Val Ser Ser Ala Ser Thr Lys Gly Pro Ser Val
               130                 135                 140
Phe Pro Leu Ala Pro Cys Ser Arg Ser Thr Ser Glu Ser Thr Ala Ala
145                 150                 155                 160
Leu Gly Cys Leu Val Lys Asp Tyr Phe Pro Glu Pro Val Thr Val Ser
               165                 170                 175
Trp Asn Ser Gly Ala Leu Thr Ser Gly Val His Thr Phe Pro Ala Val
               180                 185                 190
Leu Gln Ser Ser Gly Leu Tyr Ser Leu Ser Ser Val Val Thr Val Pro
               195                 200                 205
Ser Ser Asn Phe Gly Thr Gln Thr Tyr Thr Cys Asn Val Asp His Lys
               210                 215                 220
Pro Ser Asn Thr Lys Val Asp Lys Thr Val Glu Arg Lys Cys Cys Val
225                 230                 235                 240
Glu Cys Pro Pro Cys Pro Ala Pro Pro Val Ala Gly Pro Ser Val Phe
                    245                 250                 255
Leu Phe Pro Pro Lys Pro Lys Asp Thr Leu Met Ile Ser Arg Thr Pro
                260                 265                 270
Glu Val Thr Cys Val Val Val Asp Val Ser His Glu Asp Pro Glu Val
                275                 280                 285
Gln Phe Asn Trp Tyr Val Asp Gly Val Glu Val His Asn Ala Lys Thr
            290                 295                 300
Lys Pro Arg Glu Glu Gln Phe Asn Ser Thr Phe Arg Val Val Ser Val
305                 310                 315                 320
Leu Thr Val Val His Gln Asp Trp Leu Asn Gly Lys Glu Tyr Lys Cys
                325                 330                 335
Lys Val Ser Asn Lys Gly Leu Pro Ala Pro Ile Glu Lys Thr Ile Ser
                340                 345                 350
Lys Thr Lys Gly Gln Pro Arg Glu Pro Gln Val Tyr Thr Leu Pro Pro
                355                 360                 365
Ser Arg Glu Glu Met Thr Lys Asn Gln Val Ser Leu Thr Cys Leu Val
            370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Met Leu Asp Ser Asp
                405                 410                 415
Gly Ser Phe Phe Leu Tyr Ser Lys Leu Thr Val Asp Lys Ser Arg Trp
                420                 425                 430
Gln Gln Gly Asn Val Phe Ser Cys Ser Val Met His Glu Ala Leu His
            435                 440                 445
Asn His Tyr Thr Gln Lys Ser Leu Ser Leu Ser Pro Gly Lys
   450                 455                 460

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      Artificially synthesized primer sequence, HG2-3-437
```

```
<400> SEQUENCE: 3
gtgtaggtct gggtgccgaa gtt                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
      Artificially synthesized primer sequence, VH4-21

<400> SEQUENCE: 4
atgaaacacc tgtggttctt cct                                              23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:
      Artificially synthesized primer sequence, CG2-1

<400> SEQUENCE: 5
gctgggtgcc tgggaagtat gta                                              23
```